United States Patent [19]
Hu et al.

[11] Patent Number: 6,110,893
[45] Date of Patent: Aug. 29, 2000

[54] FIBROBLAST GROWTH FACTOR 11

[75] Inventors: Jing-Shan Hu, Gaithersburg; Craig A. Rosen, Laytonsville, both of Md.

[73] Assignee: Human Genome Sciences, Inc., Rockville, Md.

[21] Appl. No.: 09/093,585

[22] Filed: Jun. 8, 1998

Related U.S. Application Data

[62] Division of application No. 08/464,590, Jun. 5, 1995, Pat. No. 5,763,214.

[51] Int. Cl.[7] .......................... C07K 14/475; C07K 14/50; A61K 38/18
[52] U.S. Cl. .................................. 514/12; 514/2; 530/350; 530/399
[58] Field of Search ...................................... 530/350, 399; 514/2, 12

[56] References Cited

U.S. PATENT DOCUMENTS

| | | |
|---|---|---|
| 4,868,113 | 9/1989 | Jaye et al. . |
| 5,155,214 | 10/1992 | Baird et al. . |
| 5,763,214 | 6/1998 | Hu et al. . |
| 5,876,967 | 3/1999 | Nathans et al. . |

FOREIGN PATENT DOCUMENTS

| | | |
|---|---|---|
| 0 510 662 A1 | 10/1992 | European Pat. Off. . |
| 96/35716 | 11/1996 | WIPO . |
| WO96/35708 | 11/1996 | WIPO . |
| WO97/35007 | 9/1997 | WIPO . |
| WO98/08864 | 3/1998 | WIPO . |

OTHER PUBLICATIONS

Burgess et al., Annu. Rev. Biochem. 58: 575–606 (1989).
Aaronson, S.A. et al., Keratinocyte Growth Factor :62–77(1992).
Jaye, M., et al., Science, 233:541–545 (1986).
Klagsbrun, M., et al., Progress in Growth Factor. 1:207–235 (1989).
GeneSeq Accession No. T58316 (Apr. 21, 1997).
GeneSeq Accession No. T86315 (Mar. 21, 1998).
GeneSeq Accession No. V21386 (Aug. 14, 1998).
GenBank Accession No. T09003 (Aug. 3, 1993).
GenBank Accession No. T08948 (Aug. 3, 1993).
GenBank Accession No. R59031 (May 23, 1995).
Terada et al., Origins of Human Cancer: A Comprehensive Review (Brugge et al., eds.); Cold Spring Harbor, New York, 1990, pp. 675–683.
Basilico et al. (1992) Advances in Cancer Research 59:115–165.
Barinaga (1994) Science 264:772–774.
Geneseq Acc, No. Q61387 (Mar. 16, 1994).
Genbank Acc. No. Z45127 (Nov. 14, 1994).
Genbank Acc. No. M79229 (May 26, 1992).
Gospodarowicz, D., Cell Biology Reviews 25(4):307–314 (1991).

*Primary Examiner*—Marianne P. Allen
*Attorney, Agent, or Firm*—Human Genome Sciences, Inc.

[57] ABSTRACT

Disclosed is a human Fibroblast growth factor-11 polypeptide and DNA(RNA) encoding such polypeptide. Also provided is a procedure for producing such polypeptide by recombinant techniques. Also disclosed are methods for utilizing such polypeptide for promoting wound healing for example as a result of burns and ulcers, to prevent neuronal damage associated with stroke and due to neuronal disorders and promote neuronal growth, and to prevent skin aging and hair loss, to stimulate angiogenesis, mesodermal induction in early embryos and limb regeneration. Antagonists against such polypeptides and their use as a therapeutic to prevent abnormal cellular proliferation, hyper-vascular diseases and epithelial lens cell proliferation are also disclosed. Diagnostic methods for detecting mutations in the coding sequence and alterations in the concentration of the polypeptides in a sample derived from a host are also disclosed.

29 Claims, 5 Drawing Sheets

```
                                           ATGAGTGGAAAGGTGACCAAGCCCAAAGAGGAG
                                        --+---------+---------+---------+-
  1                                        M  S  G  K  V  T  K  P  K  E  E

AAAGATGCTTCTAAGGTTCTGGATGACGCCCCCCCTGGCACACAGGAATACATTATGTTA
      --+---------+---------+---------+---------+---------+---------+-
 12   K  D  A  S  K  V  L  D  D  A  P  P  G  T  Q  E  Y  I  M  L

CGACAAGATTCCATCCAATCTGCGGAATTAAAGAAAAAGAGTCCCCCTTTCGTGCTAAG
      --+---------+---------+---------+---------+---------+---------+-
 32   R  Q  D  S  I  Q  S  A  E  L  K  K  K  E  S  P  F  R  A  K

TGTCACGAAATCTTCTGCTGCCCGCTGAAGCAAGTACACCACAAAGAGAACACAGAGCCG
      --+---------+---------+---------+---------+---------+---------+-
 52   C  H  E  I  F  C  C  P  L  K  Q  V  H  H  K  E  N  T  E  P

GAAGAGCCTCAGCTTAAGGGTATAGTTACCAAGCTATACAGCCGACAAGGTACCACTTG
      --+---------+---------+---------+---------+---------+---------+-
 72   E  E  P  Q  L  K  G  I  V  T  K  L  Y  S  R  Q  G  Y  H  L

CAGCTGCAGGCGGATGGAACCATTGATGGCACCAAAGATGAGGACAGCACTTACACTCTG
      --+---------+---------+---------+---------+---------+---------+-
 92   Q  L  Q  A  D  G  T  I  D  G  T  K  D  E  D  S  T  Y  T  L

TTTAACCTCATCCCTGTGGGTCTGCGCGAGTGGTGGCTATCCAAGGAGTTCAAACCAAGCTG
      --+---------+---------+---------+---------+---------+---------+-
112   F  N  L  I  P  V  G  L  R  V  V  A  I  Q  G  V  Q  T  K  L
```

FIG.1A

```
     TACTTGGCAATGAACAGTGAGGATACTTGTACACCTGGAACTTTCACACCTGAGTGC
     ----:----+----:----+----:----+----:----+----:----+----:----+-
132  Y  L  A  M  N  S  E  G  Y  L  Y  T  S  E  L  F  T  P  E  C

AAATTCAAAGAATCAGTGTTTGAAAATTATTGTGACATATTCATCAATGATATACCGT
     ----:----+----:----+----:----+----:----+----:----+----:----+-
152  K  F  K  E  S  V  F  E  N  Y  Y  V  T  Y  S  S  M  I  Y  R

CAGCAGCAGTCAGGCCCGAGGGTGTGGATCTGGGTCTGAACAAAGAAGGAGAGATCATGAAA
     ----:----+----:----+----:----+----:----+----:----+----:----+-
172  Q  Q  Q  S  G  R  G  W  Y  L  G  L  N  K  E  G  E  I  M  K

GGCAACCATGTGAAGAAGAACAAGCCTGCAGCTCATTTTCTGCCTAAACCACTGAAAGTG
     ----:----+----:----+----:----+----:----+----:----+----:----+-
192  G  N  H  V  K  K  N  K  P  A  A  H  F  L  P  K  P  L  K  V

GCCATGTACAAGGAGCCATCACTGCACGATCTCACGGAGTTCTCCCGATCTGGAAGCGGG
     ----:----+----:----+----:----+----:----+----:----+----:----+-
212  A  M  Y  K  E  P  S  L  H  D  L  T  E  F  S  R  S  G  S  G

ACCCCAACCAAGAGCAGAAGTGTCTCTGGCGTGCTGAACGGAGGCAAATCCATGAGCCAC
     ----:----+----:----+----:----+----:----+----:----+----:----+-
232  T  P  T  K  S  R  S  V  S  G  V  L  N  G  G  K  S  M  S  H

AATGAATCAACGTAG
     ----:----+-----
252  N  E  S  T  *
```

FIG. 1B

```
                1                                                    50
Fgf-10          ..........  ..........  ..........  ..........  ..........
Fgf-11          ..........  ..........  .MSGKVTK  PKEEKDASKV  LDDAPPGTQE
Fgf-9           ..........  ..........  ..........  ..........  ..MAPLGEVG
Fgf-3           ..........  ..........  ..........  ..........  ....MGLIWL
Fgf-7           ..........  ..........  ..........  ..........  M HKWILTWILP
Fgf-1           ..........  ..........  ..........  ..........  ..........
Fgf-2           ..........  ..........  ..LGD  RGRGRALPGG  RLGGRGRGRA  PERVGGRGRG
Fgf-4           ..........  MS.GPGTAAV  ALLPAVLLAL  LA.........  .PWAGRGGAA
Fgf-6           MALGQKLFIT  MSRGAGRLQG  TLWALVFLGI  LV.........  .GMVVPSPAG
Fgf-5           ..........  ..MSL  SFLLLLFFSH  LILSAWAHGE  KRLAPKGQPG 51                                                   100
Fgf-10          ..........  ..........  ..........  ..........  .MESKEPQLK
Fgf-11          YIMLRQDSIQ  SAELKKKESP  FRAKCHEIFC  CPLKQVHHKE  NTEPEEPQLK
Fgf-9           NYFGVQDAVP  FGNVPVLPVD  SPVLLSDHLG  QSEAGGLPRG  PAVTDLDHLK
Fgf-3           LLL.......  .......SLL  EPGWPAAGPG  ARLRRDAGGR  GG.VYEHL.G
Fgf-7           TLLYRSCFHI  ICLVGTISLA  CNDMTPEQMA  TNVNCSSPER  HTRSYDYMEG
Fgf-1           ..........  ..........  ..MAEGEITT  FTALTEKFN.  ..LPPGNY..
Fgf-2           RGTAAPRAAP  AARGSRPGPA  GTMAAGSITT  LPALPEDGGS  GAFPPGHF..
Fgf-4           APTAPNGTLE  AELERRWESL  VALSLARLPV  AA..QPKEAA  VQSGAGDYLL
Fgf-6           TR.ANNTLLD  S...RGWGTL  LSRSRAGLAG  EI......AG  VNWESG.YLV
Fgf-5           PAATDRNPIG  SSSRQSSSSA  MSSSSASSSP  AASLGSQGSG  LEQSSFQWSP
```

FIG. 2A

```
            101                                                          150
Fgf-10  GIVTR..LFS QQ..GYFLQM HPDGTIDGTK DENSDYTLFN LIPVGLRVVA
Fgf-11  GIVTK..LYS RQ..GYHLQL QADGTIDGTK DEDSTYTLFN LIPVGLRVVA
Fgf-9   GILRRRQLYC RT..GFHLEI FPNGTIQGTR KDHSRFGILE FISIAVGLVS
Fgf-3   GAPRRRKLYC AT..KYHLQL HPSGRVNGSL E.NSAYSILE ITAVEVGIVA
Fgf-7   GDIRVRRLFC RT..QWYLRI DKRGKVKGTQ EMKNNYNIME IRTVAVGIVA
Fgf-1   ..KKPKLLYC SNG.GHFLRI LPDGTVDGTR DRSDQHIQLQ LSAESVGEVY
Fgf-2   ..KDPKRLYC KNG.GFFLRI HPDGRVDGVR EKSDPHIKLQ LQAEERGVVS
Fgf-4   GIKRLRRLYC NVGIGFHLQA LPDGRIGGAH A.DTRDSLLE LSPVERGVVS
Fgf-6   GIKRQRRLYC NVGIGFHLQV LPDGRISGTH E.ENPYSLLE ISTVERGVVS
Fgf-5   SGRRTGSLYC RVGIGFHLQI YPDGKVNGSH E.ANMLSVLE IFAVSQGIVG 151                                                          200
Fgf-10  IQGVKASLYV AMNGEGYLYS SDVFTPECKF KESVFENYYV IYSSTLY...
Fgf-11  IQGVQTKLYL AMNSEGYLYT SELFTPECKF KESVFENYYV TYSSMIY...
Fgf-9   IRGVDSGLYL GMNEKGELYG SEKLTQECVF REQFEENWYN TYSSNLY...
Fgf-3   IRGLFSGRYL AMNKRGRLYA SEHYSAECEF VERIHELGYN TYASRLYRTV
Fgf-7   IKGVESEFYL AMNKEGKLYA KKECNEDCNF KELILENHYN TYAS......
Fgf-1   IKSTETGQYL AMDTDGLLYG SQTPNEECLF LERLEENHYN TYISKKH...
Fgf-2   IKGVCANRYL AMKEDGRLLA SKCVTDECFF FERLESNNYN TYRSRKY...
Fgf-4   IFGVASRFFV AMSSKGKLYG SPFFTDECTF KEILLPNNYN AYESYKY...
Fgf-6   LFGVRSALFV AMNSKGRLYA TPSFQEECKF RETLLPNNYN AYESDLY...
Fgf-5   IRGVFSNKFL AMSKKGKLHA SAKFTDDCKF RERFQENSYN TYASAIH...
```

FIG. 2B

```
        201                                                          250
Fgf-10  ......RQQ  ESGRAWFLGL  NKEGQIMKG.  .NRVKKTKPS  SHFVPKPIEV
Fgf-11  ......RQQ  QSGRGWYLGL  NKEGEIMKG.  .NHVKKNKPA  AHFLPKPLKV
Fgf-9   ......KHV  DTGRRYYVAL  NKDGTPREG.  .TRTKRHQKF  THFLPRPVDP
Fgf-3   :SSTPGARRQP SAERLWYVSV  NGKGRPRRG.  .FKTRRTQKS  SLFLPRVLDH
Fgf-7   ....AKWTH   NGGEM.FVAL  NQKGIPVRG.  .KKTKKEQKT  AHFLPMAIT.
Fgf-1   .........   AEKNWFVGL   T..SWYVAL   KKNGSCKRG.  ILFLPLPVSS
Fgf-2   .........   T..SWYVAL   KRTGQYKLG.  .PRTHYGQKA  ILFLPLPVSS
Fgf-4   ......PGM   ......FIAL  SIKNKTKKG.  .SKTGPGQKA  ILFLPMSAKS
Fgf-6   ......QGT   ......YIAL  SKYGRVKRG.  .NRVSPTMKV  THFLPRL...
Fgf-5   ......RTE   KTGREWYVAL  NKRGKAKRGC  SPRVKPQHIS  THFLPRFKQS 251                                                          300
Fgf-10  CMYREPSLHE  IGEKQGRSRK  SSGTPT...   ....MNGGKV  VNQDST*...
Fgf-11  AMYKEPSLHD  LTE...FSRS  GSGTPTKSRS  VSGVLNGGKS  MSHNEST*..
Fgf-9   DKVPELYKDI  LSQS......  ..........  SPDNLEPSHV  QASRLGSQLE
Fgf-3   RDHEMVRQLQ  SGLPRPPGKG  VQPRRRRQKQ  ..........  ..........
Fgf-7   D.........  ..........  ..........  ..........  ..........
Fgf-1   ..........  ..........  ..........  ..........  ..........
Fgf-2   ..........  ..........  ..........  ..........  ..........
Fgf-4   ..........  ..........  ..........  ..........  ..........
Fgf-6   ..........  ..........  ..........  ..........  ..........
Fgf-5   EQPELSFTVT  VPEKKNPPSP  IKSKIPLSAP  RKNTNSVKYR  LKFRFG....

301
Fgf-10  ....
Fgf-11  ....
Fgf-9   :ASAH
Fgf-3   ....
Fgf-7   ....
Fgf-1   ....
Fgf-2   ....
Fgf-4   ....
Fgf-6   ....
Fgf-5   ....
```

FIG. 2C

FIBROBLAST GROWTH FACTOR 11

This application is a Divisional application entitled to priority benefits under 35 U.S.C. §120 for the information set forth in Ser. No. 08/464,590, filed Jun. 5, 1995, issued as U.S. Pat. No. 5,763,214, on Jun. 9, 1998.

This invention relates to newly identified polynucleotides, polypeptides encoded by such polynucleotides, the use of such polynucleotides and polypeptides, as well as the production of such polynucleotides and polypeptides. More particularly, the polypeptide of the present invention have been putatively identified as fibroblast growth factor/heparin binding growth factor, hereinafter referred to as "FGF-11". The invention also relates to inhibiting the action of such polypeptides.

Fibroblast growth factors are a family of proteins characteristic of binding to heparin and are, therefore, also called heparin binding growth factors (HBGF). Expression of different members of these proteins are found in various tissues and are under particular temporal and spatial control. These proteins are potent mitogens for a variety of cells of mesodermal, ectodermal, and endodermal origin, including fibroblasts, corneal and vascular endothelial cells, granulocytes, adrenal cortical cells, chondrocytes, myoblasts, vascular smooth muscle cells, lens epithelial cells, melanocytes, keratinocytes, oligodendrocytes, astrocytes, osteoblasts, and hematopoietic cells.

Each member has functions overlapping with others and also has its unique spectrum of functions. In addition to the ability to stimulate proliferation of vascular endothelial cells, both FGF-1 and 2 are chemotactic for endothelial cells and FGF-2 has been shown to enable endothelial cells to penetrate the basement membrane. Consistent with these properties, both FGF-1 and 2 have the capacity to stimulate angiogenesis. Another important feature of these growth factors is their ability to promote wound healing. Many other members of the FGF family share similar activities with FGF-1 and 2 such as promoting angiogenesis and wound healing. Several members of the FGF family have been shown to induce mesoderm formation and to modulate differentiation of neuronal cells, adipocytes and skeletal muscle cells.

Other than these biological activities in normal tissues, FGF proteins have been implicated in promoting tumorigenesis in carcinomas and sarcomas by promoting tumor vascularization and as transforming proteins when their expression is deregulated.

The FGF family presently consists of eight structurally-related polypeptides: basic FGF, acidic FGF, int 2, hst 1/k-FGF, FGF-5, FGF-6, keratinocyte growth factor, AIGF (FGF-8) and recently a glia-activating factor has been shown to be a novel heparin-binding growth factor which was purified from the culture supernatant of a human glioma cell line (Miyamoto, M. et al., Mol. and Cell. Biol., 13(7):4251–4259 (1993). The genes for each have been cloned and sequenced. Two of the members, FGF-1 and FGF-2, have been characterized under many names, but most often as acidic and basic fibroblast growth factor, respectively. The normal gene products influence the general proliferation capacity of the majority of mesoderm and neuroectoderm-derived cells. They are capable of inducing angiogenesis in vivo and may play important roles in early development (Burgess, W. H. and Maciag, T., Annu. Rev. Biochem., 58:575–606, (1989)).

Many of the above-identified members of the FGF family also bind to the same receptors and elicit a second message through binding to these receptors.

A eukaryotic expression vector encoding a secreted form of FGF-1 has been introduced by gene transfer into porcine arteries. This model defines gene function in the arterial wall in vivo. FGF-1 expression induced intimal thickening in porcine arteries 21 days after gene transfer (Nabel, E. G., et al., Nature, 362:844–6 (1993)). It has further been demonstrated that basic fibroblast growth factor may regulate glioma growth and progression independent of its role in tumor angiogenesis and that basic fibroblast growth factor release or secretion may be required for these actions (Morrison, R. S., et al., J. Neurosci. Res., 34:502–9 (1993)).

Fibroblast growth factors, such as basic FGF, have further been implicated in the growth of Kaposi's sarcoma cells in vitro (Huang, Y. Q., et al., J. Clin. Invest., 91:1191–7 (1993)). Also, the cDNA sequence encoding human basic fibroblast growth factor has been cloned downstream of a transcription promoter recognized by the bacteriophage T7 RNA polymerase. Basic fibroblast growth factors so obtained have been shown to have biological activity indistinguishable from human placental fibroblast growth factor in mitogenicity, synthesis of plasminogen activator and angiogenesis assays (Squires, C. H., et al., J. Biol. Chem., 263:16297–302 (1988)).

U.S. Pat. No. 5,155,214 discloses substantially pure mammalian basic fibroblast growth factors and their production. The amino acid sequences of bovine and human basic fibroblast growth factor are disclosed, as well as the DNA sequence encoding the polypeptide of the bovine species.

Newly discovered FGF-9 has around 30% sequence similarity to other members of the FGF family. Two cysteine residues and other consensus sequences in family members were also well conserved in the FGF-9 sequence. FGF-9 was found to have no typical signal sequence in its N terminus like those in acidic and basic FGF. However, FGF-9 was found to be secreted from cells after synthesis despite its lack of a typical signal sequence FGF (Miyamoto, M. et al., Mol. and Cell. Biol., 13(7):4251–4259 (1993). Further, FGF-9 was found to stimulate the cell growth of oligodendrocyte type 2 astrocyte progenitor cells, BALB/c3T3, and PC-12 cells but not that of human umbilical vein endothelial cells (Naruo, K., et al., J. Biol. Chem., 268:2857–2864 (1993).

Basic FGF and acidic FGF are potent modulators of cell proliferation, cell motility, differentiation, and survival and act on cell types from ectoderm, mesoderm and endoderm. These two FGFs, along with KGF and AIGF, were identified by protein purification. However, the other four members were isolated as oncogenes., expression of which was restricted to embryogenesis and certian types of cancers. FGF-9 was demonstrated to be a mitogen against glial cells. Members of the FGF family are reported to have oncogenic potency. FGF-9 has shown transforming potency when transformed into BALB/c3T3 cells (Miyamoto, M., et al., Mol. Cell. Biol., 13(7):4251–4259 (1993).

Androgen induced growth factor (AIGF), also known as FGF-8, was purified from a conditioned medium of mouse mammary carcinoma cells (SC-3) simulated with testosterone. AIGF is a distinctive FGF-like growth factor, having a putative signal peptide and sharing 30–40% homology with known members of the FGF family. Mammalian cells transformed with AIGF shows a remarkable stimulatory effect on the growth of SC-3 cells in the absence of androgen. Therefore, AIGF mediates androgen-induced growth of SC-3 cells, and perhaps other cells, since it is secreted by the tumor cells themselves.

The polypeptide of the present invention has been putatively identified as a member of the FGF family as a result of amino acid sequence homology with other members of the FGF family.

In accordance with one aspect of the present invention, there are provided novel mature polypeptides as well as biologically active and diagnostically or therapeutically useful fragments, analogs and derivatives thereof. The polypeptides of the present invention are of human origin.

In accordance with another aspect of the present invention, there are provided isolated nucleic acid molecules encoding the polypeptides of the present invention, including mRNAs, DNAs, cDNAs, genomic DNA, as well as antisense analogs thereof and biologically active and diagnostically or therapeutically useful fragments thereof.

In accordance with still another aspect of the present invention, there are provided processes for producing such polypeptides by recombinant techniques through the use of recombinant vectors, such as cloning and expression plasmids useful as reagents in the recombinant production of the polypeptides of the present invention, as well as recombinant prokaryotic and/or eukaryotic host cells comprising a nucleic acid sequence encoding a polypeptide of the present invention.

In accordance with a further aspect of the present invention, there is provided a process for utilizing such polypeptides, or polynucleotides encoding such polypeptides, for screening for agonists and antagonists thereto and for therapeutic purposes, for example, promoting wound healing for example as a result of burns and ulcers, to prevent neuronal damage associated with stroke and due to neuronal disorders and promote neuronal growth, and to prevent skin aging and hair loss, to stimulate angiogenesis, mesodermal induction in early embryos and limb regeneration.

In accordance with yet a further aspect of the present invention, there are provided antibodies against such polypeptides.

In accordance with yet another aspect of the present invention, there are provided antagonists against such polypeptides and processes for their use to inhibit the action of such polypeptides, for example, in the treatment of cellular transformation, for example, tumors, to reduce scarring and treat hyper-vascular diseases.

In accordance with another aspect of the present invention, there are provided nucleic acid probes comprising nucleic acid molecules of sufficient length to specifically hybridize to a polynucleotide encoding a polypeptide of the present invention.

In accordance with yet another aspect of the present invention, there are provided diagnostic assays for detecting diseases or susceptibility to diseases related to mutations in a nucleic acid sequence of the present invention and for detecting over-expression of the polypeptides encoded by such sequences.

In accordance with another aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are meant only as illustrations of specific embodiments of the present invention and are not meant as limitations in any manner.

FIGS. 1A and 1B collectively show the polynucleotide sequence (SEQ ID NO:1) of the cDNA encoding the mature human FGF-11 polypeptide with its deduced amino acid sequence (SEQ ID NO:2), wherein FIG. 1A illustrates the first portions of the polynucleotide sequence of the cDNA encoding the mature human FGF-11 polypeptide with its deduced amino acid sequence and FIG. 1B continues consecutively with the latter portions, respectively, up to and including the end of the same polynucleotide and amino acid sequence. The standard one-letter abbreviations for amino acid residues are used to illustrate the amino acid sequence in FIGS. 1A and 1B.

FIGS. 2A, 2B and 2C collectively show polypeptide sequences in alignment and consecutively present the alignment of the sequences to illustrate an amino acid sequence comparison between FGF-11 according to the present invention (second line of each comparative row; SEQ ID NO:2) and each of the following FGF polypeptide sequences, respectively: FGF-10 (first line of each comparative row, SEQ ID NO:9); FGF-9 (third line, SEQ ID NO:10); FGF-3 (fourth line, SEQ ID NO:11); FGF-7 (fifth line, SEQ ID NO:12); FGF-1 (sixth line, SEQ ID NO:13); FGF-2 (seventh line, SEQ ID NO:4), FGF-4 (eighth line, SEQ ID NO:15); FGF-6 (ninth line, SEQ ID NO:16) and FGF-5 (tenth line, SEQ ID NO:17). One-letter abbreviations are utilized for the amino acid residues in FIGS. 2A–2C.

In accordance with one aspect of the present invention, there are provided isolated nucleic acids molecules (polynucleotides) which encode for the mature polypeptide having the deduced amino acid sequence of FIGS. 1A–1B collectively (SEQ ID NOS:2) or for the mature polypeptide encoded by the cDNA of the clone deposited as ATCC Deposit No. 97150 on May 12, 1995 as a biological deposit with the ATCC, 10801 University Boulevard, Manassas Va. 20110-2209.

The polynucleotide encoding FGF-11 of this invention was discovered initially in a cDNA library derived from 9 week old early stage human tissue. The FGF-11 polypeptide is structurally related to all members of the fibroblast growth factor family and contains an open reading frame encoding a polypeptide of 255 amino acids. Among the top matches are: 1) 42% identity and 65% sequence similarity to FGF-9 over a stretch of 127 amino acids; 2) 37% identity and 64% similarity with FGF-7 (keratinocyte growth factor) in a region of 87 amino acids; 3) 38% identity and 64% similarity with FGF-1 (acidic FGF) over a stretch of 120 amino acids.

The FGF/HBGF family signature, GXLX(S,T,A,G)X6(D, E)CXFXE is conserved in the polypeptide of the present invention, (X means any amino acid residue; (D,E) means either D or E residue; X6 means any 6 amino acid residues).

The polynucleotide of the present invention may be in the form of RNA or in the form of DNA, which DNA includes cDNA, genomic DNA, and synthetic DNA. The DNA may be double-stranded or single-stranded. The coding sequence which encodes the mature polypeptide may be identical to the coding sequence shown in FIGS. 1A–1B collectively (SEQ ID NOS:1) or that of the deposited clone or may be a different coding sequence, as a result of the redundancy or degeneracy of the genetic code, encodes the same, mature polypeptide as the DNA of FIGS. 1A–1B, collectively, (SEQ ID NOS:1) or the deposited cDNA.

The polynucleotides which encodes for the mature polypeptide of FIGS. 1A–1B collectively (SEQ ID NOS:2) or for the mature polypeptides encoded by the deposited cDNA(s) may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptides having the deduced amino acid sequence of FIGS. 1A–1B collectively (SEQ ID NOS:2) or the polypeptides encoded by the cDNA(s) of the deposited clone(s). The variants of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1B collectively (SEQ ID NOS:2) or the same mature polypeptides encoded by the cDNA(s) of the deposited clone (s) as well as variants of such polynucleotides which variants encode for a fragment, derivative or analog of the polypeptide of FIGS. 1A–1B collectively (SEQ ID NOS:2) or the polypeptides encoded by the cDNA(s) of the deposited clone(s). Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1B, collectively (SEQ ID NOS:1) or of the coding sequence of the deposited clone(s). As known in the art, an allelic variant is an alternate form of a polynucleotide sequence which may have a substitution, deletion or addition of one or more nucleotides, which does not substantially alter the function of the encoded polypeptides.

The present invention also includes polynucleotides, wherein the coding sequence for the mature polypeptides may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotides of the present invention may encode for a mature protein, or for a protein having a prosequence or for a protein having both a prosequence and a presequence (leader sequence).

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length FGF-11 gene may be used as a hybridization probe for a cDNA library to isolate the full length gene and to isolate other genes which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete FGF-11 gene including regulatory and promotor regions, exons, and introns. An example of a screen comprises isolating the coding region of the FGF-11 gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–1B collectively (SEQ ID NO:1) or the deposited cDNA (s).

Alternatively, the polynucleotide may have at least 20 bases, preferably at least 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the Budapest Treaty on the International Recognition of the Deposit of Microorganisms for the purposes of Patent Procedure. These deposits are provided merely as a convenience and are not an admission that a deposit is required under 35 U.S.C. § 112. The sequence of the polynucleotides contained in the deposited materials, as well as the amino acid sequence of the polypeptides encoded thereby, are incorporated herein by reference and are controlling in the event of any conflict with the description of sequences herein. A license may be required to make, use or sell the deposited materials, and no such license is hereby granted.

The present invention further relates to an FGF polypeptide which has the deduced amino acid sequence of FIGS. 1A–1B, collectively (SEQ ID NOS:2) or which has the amino acid sequence encoded by the deposited cDNA(s), as well as fragments, analogs and derivatives of such polypeptides.

The terms "fragment," "derivative" and "analog" when referring to the polypeptide of FIGS. 1A–1B collectively (SEQ ID NOS:2) or those encoded by the deposited cDNA (s), means polypeptides which retains essentially the same biological function or activity as such polypeptides. Thus, an analog includes a proprotein which can be activated by cleavage of the proprotein portion to produce an active mature polypeptide.

The polypeptides of the present invention may be recombinant polypeptides, natural polypeptides or synthetic polypeptides, preferably recombinant polypeptides.

The fragment, derivative or analog of the polypeptide of FIGS. 1A–1B collectively (SEQ ID NOS:2) or that encoded by the deposited cDNA(s) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

The polypeptides of the present invention include the polypeptide of SEQ ID NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells may be genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the FGF genes. The culture conditions, such as temperature, pH and the like, are those previously used with the host cell selected for expression, and will be apparent to the ordinarily skilled artisan.

The polynucleotide of the present invention may be employed for producing a polypeptide by recombinant techniques. Thus, for example, the polynucleotide sequence may be included in any one of a variety of expression vehicles, in particular vectors or plasmids for expressing a polypeptide. Such vectors include chromosomal, nonchromosomal and synthetic DNA sequences, e.g., derivatives of SV40; bacterial plasmids; phage DNA; yeast plasmids; vectors derived from combinations of plasmids and phage DNA, viral DNA such as vaccinia, adenovirus, fowl pox virus, and pseudorabies. However, any other vector or plasmid may be used as long as they are replicable and viable in the host.

The appropriate DNA sequence may be inserted into the vector by a variety of procedures. In general, the DNA sequence is inserted into an appropriate restriction endonuclease sites by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as herein above described, as well as an appropriate promoter or control sequence, may be employed to transform an appropriate host to permit the host to express the protein. As representative examples of appropriate hosts, there may be mentioned; bacterial cells, such as *E. coli, Salmonella typhimurium*, Streltogmces; fungal cells, such as yeast; insect cells, such as Drosophila S2 and Spodoptera Sf9; animal cells such as CEO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, phagescript, psiX174, pBluescript SK, pBsKS, pNH8a, pNH16a, pNH18a, pNH46a (Stratagene); pTRC99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, 1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, (Cold Spring Harbor, N.Y., 1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promoter to increase its transcription. Examples include the SV40 enhancer on the late side of the replication origin (bp 100 to 270), a cytomegalovirus early promoter enhancer, a polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α factor, acid phosphatase, or heat shock proteins, among others. The heterologous structural sequence is assembled in appropriate phase with translation, initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation, initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., U.S.A.). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector; for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

The polypeptide of the present invention may be recovered-and purified from recombinant cell cultures by methods used heretofore, including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. Protein refolding steps can be used, as necessary, in completing configuration of the mature protein. Finally, high performance liquid chromatography (HPLC) can be employed for final purification steps.

The polypeptide of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue.

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat and prevent neuronal damage associated with stroke and which occurs in certain neuronal disorders or neuro-degenerative conditions such as Alzheimer's disease, Parkinson's disease, and AIDS-related complex. FGF-11 as the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The FGF-11 polypeptide may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The FGF-11 polypeptide may also be employed to maintain organs before transplantation or for supporting cell culture of primary tissues.

The polypeptide of the present invention may also be employed for inducing tissue of mesodermal origin to differentiate in early embryos.

In accordance with yet a further aspect of the present invention, there is provided a process for utilizing such polypeptides, or polynucleotides encoding such polypeptides, for in vitro purposes related to scientific research, synthesis of DNA, manufacture of DNA vectors and for the purpose of providing diagnostics and therapeutics for the treatment of human disease.

This invention provides a method for identification of the receptors for the polypeptides of the present invention. The genes encoding the receptor can be identified by numerous methods known to those of skill in the art, for example, ligand panning and FACS sorting (Coligan, et al., Current Protocols in Immun., 1(2), Chapter 5, (1991)). Preferably, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

This invention provides a method of screening compounds to identify those which modulate the action of the polypeptide of the present invention. An example of such an assay comprises combining a mammalian fibroblast cell, a the polypeptide of the present invention, the compound to be screened and $^3$[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of $^3$[H] thymidine in each case. The amount of fibroblast cell proliferation is measured by liquid scintillation chromatography which measures the incorporation of $^3$[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the FGF-11 receptor is measured and the ability of the compound to bind to the receptor and elicit a second messenger response is measured to determine if the compound is a potential agonist or antagonist. Such second messenger systems include but are not limited to, cAMP guanylate cyclase, tyrosine phosphorylation, ion channels or phosphoinositide hydrolysis.

Examples of antagonist compounds include antibodies, or in some cases, oligonucleotides, which bind to the receptor for the polypeptide of the present invention but elicit no second messenger response or bind to the FGF-11 polypeptide itself. Alternatively, a potential antagonist may be a mutant form of the polypeptide which binds to the receptors, however, no second messenger response is elicited and, therefore, the action of the polypeptide is effectively blocked.

Another antagonist compound to the FGF-11 gene and gene product is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of the polypeptides of the present invention. The antisense RNA oligonucleotide hybridizes to the mRNA in vivo and blocks translation of the mRNA molecule into the polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the polypeptide.

Potential antagonist compounds also include small molecules which bind to and occupy the binding site of the receptors thereby making the receptor inaccessible to its polypeptide such that normal biological activity is prevented. Examples of small molecules include, but are not limited to, small peptides or peptide-like molecules.

Antagonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonists may also be employed to prevent hypervascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonists may also be employed to prevent the growth of scar tissue during wound healing.

The antagonists may be employed in a composition with a pharmaceutically acceptable carrier, e.g., as hereinafter described.

The polypeptides, agonists and antagonists of the present invention may be employed in combination with a suitable pharmaceutical carrier to comprise a pharmaceutical composition for parenteral administration. Such compositions comprise a therapeutically effective amount of the polypeptide, agonist or antagonist and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides, agonists and antagonists of the present invention may be employed in conjunction with other therapeutic compounds.

The pharmaceutical compositions may be administered in a convenient maimer such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc. In the specific case of topical administration, dosages are preferably administered from about 0.1 $\mu$g to 9 mg per cm$^2$.

The polypeptide of the invention and agonist and antagonist compounds which are polypeptides, may also be employed in accordance with the present invention by expression of such polypeptide in vivo, which is often referred to as "gene therapy."

Thus, for example, cells may be engineered with a polynucleotide (DNA or RNA) encoding for the polypeptide ex vivo, the engineered cells are then provided to a patient to be treated with the polypeptide. Such methods are well-known in the art. For example, cells may be engineered by procedures known in the art by use of a retroviral particle containing RNA encoding for the polypeptide of the present invention.

Similarly, cells may be engineered in vivo for expression of the polypeptide in vivo, for example, by procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such methods should be apparent to those skilled in the art from the teachings of the present invention. For example, the expression vehicle for engineering cells may be other than a retroviral particle, for example, an adenovirus, which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CTV) promoter described in Miller, et al., *Biotechnipues*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CKV) promoter; the respiratory syncytial-virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PES501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence (s) encoding the polypeptides. Such retroviral vector particles then may be employed, to transduce eukaryotic cells, either in vitro or in vivo. The transduced eukaryotic cells will express the nucleic acid sequencers) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the genes of the present invention as part of a diagnostic assay for detecting diseases or susceptibility to diseases related to the presence of mutations in the nucleic acid sequences encoding the polypeptide of the present invention.

Individuals carrying mutations in a gene of the present invention may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding a polypeptide of the present invention can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, U.S.A., 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of FGF-11 proteins in various tissues since an over-expression of the proteins compared to normal control tissue samples may detect the presence of abnormal cellular proliferation, for example, a tumor. Assays used to detect levels of protein in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, (1991)) initially comprises preparing an antibody specific to an antigen to the polypeptides of the present invention, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like bovine serum albumen. Next, the monoclonal antibody is incubated in the dish during which time the monoclonal antibodies attach to any polypeptides of the present invention attached to the polystyrene dish. All unbound monoclonal antibody is washed out with buffer. The reporter antibody linked to horseradish peroxidase is now placed in the dish resulting in binding of the reporter antibody to any monoclonal antibody bound to the protein of interest.

Unattached reporter antibody is then washed out. Peroxidase substrates are then added to the dish and the amount of color developed in a given time period is a measurement of the amount of a polypeptide of the present invention present in a given volume of patient sample when compared against a standard curve.

A competition assay may be employed wherein antibodies specific to a polypeptide of the present invention are attached to a solid support and labeled FGF-11 and a sample derived from the host are passed over the solid support and the amount of label detected, for example by liquid scintillation chromatography, can be correlated to a quantity of a polypeptide of the present invention in the sample.

A "sandwich" assay is similar to an ELISA assay. In a "sandwich" assay a polypeptide of the present invention is passed over a solid support and binds to antibody attached to a solid support. A second antibody is then bound to the polypeptide of interest. A third antibody which is labeled and specific to the second antibody is then passed over the solid support and binds to the second antibody and an amount can then be quantified.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphism's) are presently available for marking chromosomal location. The mapping of DHAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. (Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples, certain-frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by t he manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equiuolar amounts of the DNA fragments to be ligated.

Unless otherwise stated, transformation was performed as described by the method of Graham, P. and Van der Eb, A., Virology, 52:456–457 (1973).

EXAMPLE 1

Bacterial Expression and Purification of FGF-11 Proteins

The DNA sequence encoding FGF-11, ATCC # 97150, is initially amplified using PCR oligonucleotide primers corresponding to the 5' sequences of the processed protein (minus the signal peptide sequence) and the vector sequences 3' to the gene. Additional nucleotides corresponding to the gene are added to the 5' and 3' sequences respectively. The 5' oligonucleotide primer 5' CGCGGATCCATCATGAGTGGAAAGGTGACCAAG 3' (SEQ ID NO:3) contains a BamHI restriction enzyme site. The 3' sequence 5' CGCGGATCCCGTTGATTCATTGTGGCTCAT 3' (SEQ ID NO:4) contains complementary sequences to a BamHI site and is followed by 21 nucleotides of FGF-11 coding sequence.

The restriction enzyme sites correspond to the restriction enzyme sites on the bacterial expression vector pQE-60 (Qiagen, Inc. Chatsworth, Calif. 91311). pQE-60 encodes antibiotic resistance (Ampr), a bacterial origin of replication (ori), an IPTG-regulatable promoter operator (P/O), a ribosome binding site (RBS), a 6-His tag and restriction enzyme sites. pQE-60 was then digested with NcoI and BamHI. The amplified sequences are ligated into pQE-60 and are inserted in frame with the sequence encoding for the histidine tag and the ribosome binding site (RBS). The ligation mixture is then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the lacI repressor and also confers kanamycin resistance (Kan'). Transformants are identified by their ability to grow on LB plates and ampicillin/kanamycin resistant colonies were selected. Plasmid DNA is isolated and confirmed by restriction analysis. Clones containing the desired constructs are grown overnight (O/N) in liquid culturein LB media supplemented with both Amp (100 μg/ml) and Kan (25 μg/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells a re grown an extra 3 to 4 hours. Cells are then harvested by centrifugation. The cell pellet is solubilized in the chaotropic agent 6 Molar Guanidine HCl. After clarification, solubilized FGF-11 is purified from this solution by chromatography on a Nickel-NAT resin under conditions that allow for tight binding by proteins containing the 5-His tag (Hochuli, E. et al.S , J. Chromatography 411:177–184 (1984)) . The proteins are eluted from the column in 6 molar guanidine HCl pH 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the proteins are dialyzed to 10 mmolar sodium phosphate.

EXAMPLE 2

Expression of FGF-11 by in vitro Transcription and Translation.

The FGF-11 cDNA, ATCC # 97150, was transcribed and translated in vitro to determine the size of the translatable polypeptide encoded by the full length FGF-11 cDNA. The full length cDNA inserts of FGF-11 in the pbluescript SK vector.

The in vitro transcription/translation reaction was performed in a 25 ul volume, using the $T_NT$™ Coupled Reticulocylae Lysate Systems (Promega, CAT# L4950). Specifically, the reaction contains 12.5 ul of $T_NT$ rabbit reticulocyte lysate, 2 μl of $T_NT$ reaction buffer, 1 μl of T3 polymerase, 1 μl of 1 mM amino acid mixture (minus methionine), 4 μl of $^{35}$S-methionine (>1000 Ci/mmol, 10 mCi/ml), 1 μl of 40 U/μl; RNasin ribonuclease inhibitor, 0.5 or 1 μg of pBluescript FGF-11 plasmid. Nuclease-free H$_2$O was added to bring the volume to 25 ul. The reaction was incubated at 30° C. for 2 hours . Five microliters of the reaction product was analyzed on a 4–20% gradient SDS-PAGE gel. After fixing in 25% isopropanol and 10% acetic acid, the gel was dried and exposed to an X-ray film overnight at 70° C.

EXAMPLE 3

Cloning and Expression of FGF-11 Using the Baculovirus Expression System

The DNA sequence encoding the full length FGF-11 protein, ATCC # 97150, is amplified using PCR oligonucleotide primers corresponding to the 5' and 3' sequences of the gene:

The FGF-11 5' primer has the sequence 5' CGCGGATCCATCATG AGTGGAAAGGTGACCAAG 3' (SEQ ID NO:5) and contains a BamHI restriction enzyme site (in bold) such that cloning at this site will put the baculovirus signal sequence in frame with 21 nucleotides of the FGF-11 gene downstream of the putative FGF-11 signal peptide cleavage site.

The 3' primer has the sequence 5' CGCGGTAC-CCTACGTTGA TTCATTGTGGCT 3' (SEQ ID NO:6) and contains the cleavage site for the restriction endonuclease Asp718 and 21 nucleotides complementary to the 3' non-translated sequence of the gene.

The amplified sequences are isolated from a 1% agarose gel using a commercially available kit ("Geneclean," BIO 101 Inc., La Jolla, Calif.). The fragment is then digested with the respective endonucleases and purified again on a 1% agarose gel. This fragment is designated F2.

The vector pA2 (modification of pVL941 vector, discussed below) is used for the expression of the proteins using the baculovirus expression system (for review see: Summers, M.D. and Smith, G.E. 1987, A manual of methods for baculovirus vectors and insect cell culture procedures, Texas Agricultural Experimental Station Bulletin No. 1555). This expression vector contains the strong polyhedrin promoter of the *Autographa californica* nuclear polyhedrosis virus (AcMNPV) followed by the recognition sites for the restriction endonucleases BamHI and Asp718. The polyadenylation site of the simian virus (SV)40 is used for efficient polyadenylation. For an easy selection of recombinant virus the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pA2 such as pRG1, pAc373, pVL941 and pAcIM1 (Luckow, V. A. and Summers, M. D., Virology, 170:31–39).

The plasmid is digested with the restriction enzymes and dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. *E.coli* DH5α cells are then transformed and bacteria identified that contained the plasmid (pBacFGF-11) using the respective restriction enzymes. The sequence of the cloned fragment are confirmed by DNA sequencing.

5 μg of the plasmid pBacFGF-11 are co-transtected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. U.S.A., 84:7413–7417 (1987)).

1 μg of BaculoGold™ virus DNA and 5 μg of the plasmids, in each case, are mixed in a sterile well of microtiter plates containing 50 μl of serum free Grace's medium (Life Technologies Inc., Gaithersburg, Md.). Afterwards 10 μl Lipofectin plus 90 μl Grace's medium are added, mixed and incubated for 15 minutes at room temperature. Then the transfection mixture is added drop-wise to the Sf9 insect cells (ATCC CRL 1711) seeded in 35 mm tissue culture plates with 1 ml Grace's medium without serum. The plates are rocked back and forth to mix the newly added solution. The plates are then incubated for 5 hours at 27° C. After 5 hours the transfection solution is removed from the plate and 1 ml of Grace's insect medium supplemented with 10% fetal calf serum is added. The plates are put back into an incubator and cultivation continued at 27° C. for four days.

After four days the supernatant is collected and plaque assays performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution the virus is added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-FGF-11 at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labelled proteins visualized by SDS-PAGE and autoradiography.

EXAMPLE 4

Expression of Recombinant FGF-11 in COS Cells

The expression of plasmids, FGF-11-HA derived from a vector pcDNA3/Amp (Invitrogen) containing: 1) SV40 origin of replication, 2) ampicillin resistance gene, 3) *E. coli* replication origin, 4) CKV promoter followed by a polylinker region, an SV40 intron and polyadenylation site. DNA fragments encoding the entire FGF-11 precursor and an HA tag fused in frame to the 3' end is cloned into the polylinker region of the vector, therefore, the recombinant protein expression is directed under the CKV promoter. The HA tag corresponds to an epitope derived from the influenza hemagglutinin protein as previously described (I. Wilson, H. Niman, R. Heighten, A Cherenson, M. Connolly, and R. Lerner, 1984, Cell 37:767, (1984)). The infusion of HA tag to the target protein allows easy detection of the recombinant protein with an antibody that recognizes the HA epitope.

The plasmid construction strategy is described as follows:

The DNA sequence encoding FGF-11, ATCC # 97150, is constructed by PCR using two primers: the 5' primer 5' CGCGGATCCATCATGAGTGGAAAGGTGACCAAG 3' (SEQ ID NO:7) contains a BamHI site followed by 21 nucleotides of coding sequence starting from the initiation codon; the 3' sequence 5' CTCGAG CGTTGATTCAT-TGTGGCTCAT 3' (SEQ ID NO:8) contains complementary sequences to an XbaI site and the last 21 nucleotides of the FGF-11 coding sequence (not including the stop codon). Therefore, the PCR product contains a XhoI site, coding sequence followed by HA tag fused in frame, a translation termination stop codon next to the HA tag, and an XhoI site.

The PCR amplified DNA fragments and the vector, pcDNA3/Amp, are digested with the respective restriction enzymes and ligated. The ligation mfixture is transformed into *E. coli* strain SURE (available from Stratagene Cloning Systems, La Jolla, Calif. 92037) the transformed culture is plated on ampicillin media plates and resistant colonies are seleted. Plasstid DNA is isolated from transformants and examined by restriction analysis for the presence of the correct fragment. For expression of the recombinant FGF-11 COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the FGF-11-HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media is then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984) Both cell lysate and culture media are precipitated with a n HA specific monoclonal antibody. Proteins precipitated are analyzed on 15% SDS-PAGE gels.

EXAMPLE 5

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temerature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbeccol's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging ceils are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polypeptide comprising an amino acid sequence selected from the group consisting of:
   (a) amino acid residues 1 to 255 of SEQ ID NO:2;
   (b) amino acid residues 2 to 255 of SEQ ID NO:2;
   (c) at least 30 contiguous amino acid residues of SEQ ID NO:2;
   (d) the amino acid sequence of the polypeptide encoded by the human cDNA contained in ATCC Deposit No. 97150;
   (e) at least 30 contiguous amino acid residues of the polypeptide encoded by the human cDNA contained in ATCC Deposit No. 97150;
   (f) the amino acid sequence of a fragment of the polypeptide shown as amino acid residues 1 to 255 of SEQ ID NO:2 wherein said fragment has fibroblast growth factor activity; and
   (g) the amino acid sequence of a fragment of the polypeptide encoded by the human cDNA contained in ATCC Deposit No. 97150 wherein said fragment has fibroblast growth factor activity.

2. The isolated polypeptide of claim 1 wherein the amino acid sequence is (c).

3. The isolated polypeptide of claim 2 wherein the polypeptide comprises amino acid residues 2 to 255 of SEQ ID NO:2.

4. The isolated polypeptide of claim 3 wherein the polypeptide comprises amino acid residues 1 to 255 of SEQ ID NO:2.

5. A composition comprising the isolated polypeptide of claim 4 in a pharmaceutically acceptable carrier.

6. An isolated polypeptide produced by the method comprising:
   (a) expressing the polypeptide of claim 4 from a host cell; and
   (b) recovering said polypeptide.

7. A composition comprising the isolated polypeptide of claim 3 in a pharmaceutically acceptable carrier.

8. An isolated polypeptide produced by the method comprising:
   (a) expressing the polypeptide of claim 3 from a host cell; and
   (b) recovering said polypeptide.

9. The isolated polypeptide of claim 2 wherein the polypeptide comprises at least 50 contiguous amino acid residues of SEQ ID NO:2.

10. A composition comprising the isolated polypeptide of claim 9 in a pharmaceutically acceptable carrier.

11. An isolated polypeptide produced by the method comprising:
    (a) expressing the polypeptide of claim 9 from a host cell; and
    (b) recovering said polypeptide.

12. A composition comprising the isolated polypeptide of claim 2 in a pharmaceutically acceptable carrier.

13. The isolated polypeptide of claim 1 wherein the amino acid sequence is (e).

14. The isolated polypeptide of claim 13 wherein the polypeptide comprises the amino acid sequence of the polypeptide encoded by the human cDNA contained in ATCC Deposit No. 97150.

15. A composition comprising the isolated polypeptide of claim 14 in a pharmaceutically acceptable carrier.

16. An isolated polypeptide produced by the method comprising:
    (a) expressing the polypeptide of claim 14 from a host cell; and
    (b) recovering said polypeptide.

17. A composition comprising the isolated polypeptide of claim 13 in a pharmaceutically acceptable carrier.

18. An isolated polypeptide produced by the method comprising:
    (a) expressing the polypeptide of claim 3 from a host cell; and
    (b) recovering said polypeptide.

19. The isolated polypeptide of claim 1 fused to a heterologous polypeptide.

20. A composition comprising the isolated polypeptide of claim 19 in a pharmaceutically acceptable carrier.

21. An isolated polypeptide produced by the method comprising:
    (a) expressing the polypeptide of claim 19 from a host cell; and
    (b) recovering said polypeptide.

22. The isolated polypeptide of claim 1 wherein the amino acid sequence is (f).

23. A composition comprising the isolated polypeptide of claim 22 in a pharmaceutically acceptable carrier.

24. An isolated polypeptide produced by the method comprising:
    (a) expressing the polypeptide of claim 22 from a host cell; and
    (b) recovering said polypeptide.

25. The isolated polypeptide of claim 1 wherein the amino acid sequence is (g).

26. A composition comprising the isolated polypeptide of claim 25 in a pharmaceutically acceptable carrier.

27. An isolated polypeptide produced by the method comprising:
    (a) expressing the polypeptide of claim 25 from a host cell; and
    (b) recovering said polypeptide.

28. A composition comprising the isolated polypeptide of claim 1 in a pharmaceutically acceptable carrier.

29. An isolated polypeptide produced by the method comprising:
    (a) expressing the polypeptide of claim 2 from a host cell; and
    (b) recovering said polypeptide.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 768 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..765

(xi) SEQUENCE DESCRIPTION: SEQ ID NO:1:

| | | | | | | | | | | | | | | | | |
|---|---|---|---|---|---|---|---|---|---|---|---|---|---|---|---|---|
| ATG | AGT | GGA | AAG | GTG | ACC | AAG | CCC | AAA | GAG | GAG | AAA | GAT | GCT | TCT | AAG | 48 |
| Met | Ser | Gly | Lys | Val | Thr | Lys | Pro | Lys | Glu | Glu | Lys | Asp | Ala | Ser | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GTT | CTG | GAT | GAC | GCC | CCC | CCT | GGC | ACA | CAG | GAA | TAC | ATT | ATG | TTA | CGA | 96 |
| Val | Leu | Asp | Asp | Ala | Pro | Pro | Gly | Thr | Gln | Glu | Tyr | Ile | Met | Leu | Arg | |
| | | | 20 | | | | | 25 | | | | | 30 | | | |

| | | | | | | | | | | | | | | | | |
|---|---|---|---|---|---|---|---|---|---|---|---|---|---|---|---|---|
| CAA | GAT | TCC | ATC | CAA | TCT | GCG | GAA | TTA | AAG | AAA | AAA | GAG | TCC | CCC | TTT | 144 |
| Gln | Asp | Ser | Ile | Gln | Ser | Ala | Glu | Leu | Lys | Lys | Lys | Glu | Ser | Pro | Phe | |
| | | 35 | | | | | 40 | | | | | 45 | | | | |

| | | | | | | | | | | | | | | | | |
|---|---|---|---|---|---|---|---|---|---|---|---|---|---|---|---|---|
| CGT | GCT | AAG | TGT | CAC | GAA | ATC | TTC | TGC | TGC | CCG | CTG | AAG | CAA | GTA | CAC | 192 |
| Arg | Ala | Lys | Cys | His | Glu | Ile | Phe | Cys | Cys | Pro | Leu | Lys | Gln | Val | His | |
| | 50 | | | | | 55 | | | | | 60 | | | | | |

| | | | | | | | | | | | | | | | | |
|---|---|---|---|---|---|---|---|---|---|---|---|---|---|---|---|---|
| CAC | AAA | GAG | AAC | ACA | GAG | CCG | GAA | GAG | CCT | CAG | CTT | AAG | GGT | ATA | GTT | 240 |
| His | Lys | Glu | Asn | Thr | Glu | Pro | Glu | Glu | Pro | Gln | Leu | Lys | Gly | Ile | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ACC | AAG | CTA | TAC | AGC | CGA | CAA | GGC | TAC | CAC | TTG | CAG | CTG | CAG | GCG | GAT | 288 |
| Thr | Lys | Leu | Tyr | Ser | Arg | Gln | Gly | Tyr | His | Leu | Gln | Leu | Gln | Ala | Asp | |
| | | | | 85 | | | | | 90 | | | | | 95 | | |

| | | | | | | | | | | | | | | | | |
|---|---|---|---|---|---|---|---|---|---|---|---|---|---|---|---|---|
| GGA | ACC | ATT | GAT | GGC | ACC | AAA | GAT | GAG | GAC | AGC | ACT | TAC | ACT | CTG | TTT | 336 |
| Gly | Thr | Ile | Asp | Gly | Thr | Lys | Asp | Glu | Asp | Ser | Thr | Tyr | Thr | Leu | Phe | |
| | | | 100 | | | | | 105 | | | | | 110 | | | |

| | | | | | | | | | | | | | | | | |
|---|---|---|---|---|---|---|---|---|---|---|---|---|---|---|---|---|
| AAC | CTC | ATC | CCT | GTG | GGT | CTG | CGA | GTG | GTG | GCT | ATC | CAA | GGA | GTT | CAA | 384 |
| Asn | Leu | Ile | Pro | Val | Gly | Leu | Arg | Val | Val | Ala | Ile | Gln | Gly | Val | Gln | |
| | | 115 | | | | | 120 | | | | | 125 | | | | |

| | | | | | | | | | | | | | | | | |
|---|---|---|---|---|---|---|---|---|---|---|---|---|---|---|---|---|
| ACC | AAG | CTG | TAC | TTG | GCA | ATG | AAC | AGT | GAG | GGA | TAC | TTG | TAC | ACC | TCG | 432 |
| Thr | Lys | Leu | Tyr | Leu | Ala | Met | Asn | Ser | Glu | Gly | Tyr | Leu | Tyr | Thr | Ser | |
| | 130 | | | | | 135 | | | | | 140 | | | | | |

| | | | | | | | | | | | | | | | | |
|---|---|---|---|---|---|---|---|---|---|---|---|---|---|---|---|---|
| GAA | CTT | TTC | ACA | CCT | GAG | TGC | AAA | TTC | AAA | GAA | TCA | GTG | TTT | GAA | AAT | 480 |
| Glu | Leu | Phe | Thr | Pro | Glu | Cys | Lys | Phe | Lys | Glu | Ser | Val | Phe | Glu | Asn | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| TAT | TAT | GTG | ACA | TAT | TCA | TCA | ATG | ATA | TAC | CGT | CAG | CAG | CAG | TCA | GGC | 528 |
| Tyr | Tyr | Val | Thr | Tyr | Ser | Ser | Met | Ile | Tyr | Arg | Gln | Gln | Gln | Ser | Gly | |
| | | | | 165 | | | | | 170 | | | | | 175 | | |

| | | | | | | | | | | | | | | | | |
|---|---|---|---|---|---|---|---|---|---|---|---|---|---|---|---|---|
| CGA | GGG | TGG | TAT | CTG | GGT | CTG | AAC | AAA | GAA | GGA | GAG | ATC | ATG | AAA | GGC | 576 |
| Arg | Gly | Trp | Tyr | Leu | Gly | Leu | Asn | Lys | Glu | Gly | Glu | Ile | Met | Lys | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| AAC | CAT | GTG | AAG | AAG | AAC | AAG | CCT | GCA | GCT | CAT | TTT | CTG | CCT | AAA | CCA | 624 |
| Asn | His | Val | Lys | Lys | Asn | Lys | Pro | Ala | Ala | His | Phe | Leu | Pro | Lys | Pro | |
| | | 195 | | | | | 200 | | | | | 205 | | | | |

| | | | | | | | | | | | | | | | | |
|---|---|---|---|---|---|---|---|---|---|---|---|---|---|---|---|---|
| CTG | AAA | GTG | GCC | ATG | TAC | AAG | GAG | CCA | TCA | CTG | CAC | GAT | CTC | ACG | GAG | 672 |
| Leu | Lys | Val | Ala | Met | Tyr | Lys | Glu | Pro | Ser | Leu | His | Asp | Leu | Thr | Glu | |
| | 210 | | | | | 215 | | | | | 220 | | | | | |

| | | | | | | | | | | | | | | | | |
|---|---|---|---|---|---|---|---|---|---|---|---|---|---|---|---|---|
| TTC | TCC | CGA | TCT | GGA | AGC | GGG | ACC | CCA | ACC | AAG | AGC | AGA | AGT | GTC | TCT | 720 |
| Phe | Ser | Arg | Ser | Gly | Ser | Gly | Thr | Pro | Thr | Lys | Ser | Arg | Ser | Val | Ser | |
| 225 | | | | | 230 | | | | | 235 | | | | | 240 | |

| | | | | | | | | | | | | | | |
|---|---|---|---|---|---|---|---|---|---|---|---|---|---|---|
| GGC | GTG | CTG | AAC | GGA | GGC | AAA | TCC | ATG | AGC | CAC | AAT | GAA | TCA | ACG | 765 |
| Gly | Val | Leu | Asn | Gly | Gly | Lys | Ser | Met | Ser | His | Asn | Glu | Ser | Thr | |
| | | | | 245 | | | | | 250 | | | | | 255 | |

TAG                                                                  768

(2) INFORMATION FOR SEQ ID NO:2:

(i) SEQUENCE CHARACTERISTICS:
        (A) LENGTH: 255 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ser Gly Lys Val Thr Lys Pro Lys Glu Lys Asp Ala Ser Lys
 1               5                  10                  15

Val Leu Asp Asp Ala Pro Pro Gly Thr Gln Glu Tyr Ile Met Leu Arg
             20                  25                  30

Gln Asp Ser Ile Gln Ser Ala Glu Leu Lys Lys Lys Glu Ser Pro Phe
             35                  40                  45

Arg Ala Lys Cys His Glu Ile Phe Cys Cys Pro Leu Lys Gln Val His
         50                  55                  60

His Lys Glu Asn Thr Glu Pro Glu Pro Gln Leu Lys Gly Ile Val
 65              70                  75                  80

Thr Lys Leu Tyr Ser Arg Gln Gly Tyr His Leu Gln Leu Gln Ala Asp
             85                  90                  95

Gly Thr Ile Asp Gly Thr Lys Asp Glu Asp Ser Thr Tyr Thr Leu Phe
            100                 105                 110

Asn Leu Ile Pro Val Gly Leu Arg Val Val Ala Ile Gln Gly Val Gln
            115                 120                 125

Thr Lys Leu Tyr Leu Ala Met Asn Ser Glu Gly Tyr Leu Tyr Thr Ser
130                 135                 140

Glu Leu Phe Thr Pro Glu Cys Lys Phe Lys Glu Ser Val Phe Glu Asn
145                 150                 155                 160

Tyr Tyr Val Thr Tyr Ser Ser Met Ile Tyr Arg Gln Gln Gln Ser Gly
                165                 170                 175

Arg Gly Trp Tyr Leu Gly Leu Asn Lys Glu Gly Glu Ile Met Lys Gly
                180                 185                 190

Asn His Val Lys Lys Asn Lys Pro Ala Ala His Phe Leu Pro Lys Pro
            195                 200                 205

Leu Lys Val Ala Met Tyr Lys Glu Pro Ser Leu His Asp Leu Thr Glu
210                 215                 220

Phe Ser Arg Ser Gly Ser Gly Thr Pro Thr Lys Ser Arg Ser Val Ser
225                 230                 235                 240

Gly Val Leu Asn Gly Gly Lys Ser Met Ser His Asn Glu Ser Thr
                245                 250                 255

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CGCGGATCCA TCATGAGTGG AAAGGTGACC AAG                          33

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

CGCGGATCCC GTTGATTCAT TGTGGCTCAT                              30
```

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

CGCGGATCCA TCATGAGTGG AAAGGTGACC AAG                            33

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CGCGGTACCC TACGTTGATT CATTGTGGCT                                30

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CGCGGATCCA TCATGAGTGG AAAGGTGACC AAG                            33

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CTCGAGCGTT GATTCATTGT GGCTCAT                                    27

(2) INFORMATION FOR SEQ ID NO:9:

(i) SEQUENCE CHARACTERISTICS:
        (A) LENGTH: 181 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

```
Met Glu Ser Lys Glu Pro Gln Leu Lys Gly Ile Val Thr Arg Leu Phe
1               5                   10                  15
Ser Gln Gln Gly Tyr Phe Leu Gln Met His Pro Asp Gly Thr Ile Asp
            20                  25                  30
```

```
Gly Thr Lys Asp Glu Asn Ser Asp Tyr Thr Leu Phe Asn Leu Ile Pro
        35                  40                  45

Val Gly Leu Arg Val Val Ala Ile Gln Gly Val Lys Ala Ser Leu Tyr
 50                  55                  60

Val Ala Met Asn Gly Glu Gly Tyr Leu Tyr Ser Ser Asp Val Phe Thr
 65                  70                  75                  80

Pro Glu Cys Lys Phe Lys Glu Ser Val Phe Glu Asn Tyr Tyr Val Ile
                 85                  90                  95

Tyr Ser Ser Thr Leu Tyr Arg Gln Gln Glu Ser Gly Arg Ala Trp Phe
                100                 105                 110

Leu Gly Leu Asn Lys Glu Gly Gln Ile Met Lys Gly Asn Arg Val Lys
            115                 120                 125

Lys Thr Lys Pro Ser Ser His Phe Val Pro Lys Pro Ile Glu Val Cys
        130                 135                 140

Met Tyr Arg Glu Pro Ser Leu His Glu Ile Gly Glu Lys Gln Gly Arg
145                 150                 155                 160

Ser Arg Lys Ser Ser Gly Thr Pro Thr Met Asn Gly Gly Lys Val Val
                165                 170                 175

Asn Gln Asp Ser Thr
            180

(2) INFORMATION FOR SEQ ID NO:10:

(i) SEQUENCE CHARACTERISTICS:
        (A) LENGTH: 208 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Met Ala Pro Leu Gly Glu Val Gly Asn Tyr Phe Gly Val Gln Asp Ala
 1               5                  10                  15

Val Pro Phe Gly Asn Val Pro Val Leu Pro Val Asp Ser Pro Val Leu
                20                  25                  30

Leu Ser Asp His Leu Gly Gln Ser Glu Ala Gly Gly Leu Pro Arg Gly
            35                  40                  45

Pro Ala Val Thr Asp Leu Asp His Leu Lys Gly Ile Leu Arg Arg Arg
 50                  55                  60

Gln Leu Tyr Cys Arg Thr Gly Phe His Leu Glu Ile Phe Pro Asn Gly
 65                  70                  75                  80

Thr Ile Gln Gly Thr Arg Lys Asp His Ser Arg Phe Gly Ile Leu Glu
                 85                  90                  95

Phe Ile Ser Ile Ala Val Gly Leu Val Ser Ile Arg Gly Val Asp Ser
                100                 105                 110

Gly Leu Tyr Leu Gly Met Asn Glu Lys Gly Glu Leu Tyr Gly Ser Glu
            115                 120                 125

Lys Leu Thr Gln Glu Cys Val Phe Arg Glu Gln Phe Glu Glu Asn Trp
        130                 135                 140

Tyr Asn Thr Tyr Ser Ser Asn Leu Tyr Lys His Val Asp Thr Gly Arg
145                 150                 155                 160

Arg Tyr Tyr Phe Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190
```

```
Asp Pro Asp Lys Val Pro Glu Leu Tyr Lys Asp Ile Leu Ser Gln Ser
            195                 200                 205
```

(2) INFORMATION FOR SEQ ID NO:11:

(i) SEQUENCE CHARACTERISTICS:
        (A) LENGTH: 239 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
Met Gly Leu Ile Trp Leu Leu Leu Ser Leu Leu Glu Pro Gly Trp
1               5                   10                  15

Pro Ala Ala Gly Pro Gly Ala Arg Leu Arg Arg Asp Ala Gly Gly Arg
                20                  25                  30

Gly Gly Val Tyr Glu His Leu Gly Gly Ala Pro Arg Arg Arg Lys Leu
            35                  40                  45

Tyr Cys Ala Thr Lys Tyr His Leu Gln Leu His Pro Ser Gly Arg Val
        50                  55                  60

Asn Gly Ser Leu Glu Asn Ser Ala Tyr Ser Ile Leu Glu Ile Thr Ala
65                  70                  75                  80

Val Glu Val Gly Ile Val Ala Ile Arg Gly Leu Phe Ser Gly Arg Tyr
                85                  90                  95

Leu Ala Met Asn Lys Arg Gly Arg Leu Tyr Ala Ser Glu His Tyr Ser
                100                 105                 110

Ala Glu Cys Glu Phe Val Glu Arg Ile His Glu Leu Gly Tyr Asn Thr
            115                 120                 125

Tyr Ala Ser Arg Leu Tyr Arg Thr Val Ser Ser Thr Pro Gly Ala Arg
        130                 135                 140

Arg Gln Pro Ser Ala Glu Arg Leu Trp Tyr Val Ser Val Asn Gly Lys
145                 150                 155                 160

Gly Arg Pro Arg Arg Gly Phe Lys Thr Arg Arg Thr Gln Lys Ser Ser
                165                 170                 175

Leu Phe Leu Pro Arg Val Leu Asp His Arg Asp His Glu Met Val Arg
                180                 185                 190

Gln Leu Gln Ser Gly Leu Pro Arg Pro Pro Gly Lys Gly Val Gln Pro
            195                 200                 205

Arg Arg Arg Arg Gln Lys Gln Ser Pro Asp Asn Leu Glu Pro Ser His
            210                 215                 220

Val Gln Ala Ser Arg Leu Gly Ser Gln Leu Glu Ala Ser Ala His
225                 230                 235
```

(2) INFORMATION FOR SEQ ID NO:12:

(i) SEQUENCE CHARACTERISTICS:
        (A) LENGTH: 194 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30
```

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
 50                  55                  60

Arg Val Arg Arg Leu Phe Cys Arg Thr Gln Trp Tyr Leu Arg Ile Asp
 65                  70                  75                  80

Lys Arg Gly Lys Val Lys Gly Thr Gln Glu Met Lys Asn Asn Tyr Asn
                 85                  90                  95

Ile Met Glu Ile Arg Thr Val Ala Val Gly Ile Val Ala Ile Lys Gly
            100                 105                 110

Val Glu Ser Glu Phe Tyr Leu Ala Met Asn Lys Glu Gly Lys Leu Tyr
            115                 120                 125

Ala Lys Lys Glu Cys Asn Glu Asp Cys Asn Phe Lys Glu Leu Ile Leu
130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
                180                 185                 190

Ile Thr (2) INFORMATION FOR SEQ ID NO:13:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Met Ala Glu Gly Glu Ile Thr Thr Phe Thr Ala Leu Thr Glu Lys Phe
 1                   5                  10                  15

Asn Leu Pro Pro Gly Asn Tyr Lys Lys Pro Lys Leu Leu Tyr Cys Ser
                 20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
 50                  55                  60

Ser Val Gly Glu Val Tyr Ile Lys Ser Thr Glu Thr Gly Gln Tyr Leu
 65                  70                  75                  80

Ala Met Asp Thr Asp Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
            115                 120                 125

Asn Gly Ser Cys Lys Arg Gly Pro Arg Thr His Tyr Gly Gln Lys Ala
130                 135                 140

Ile Leu Phe Leu Pro Leu Pro Val Ser Ser Asp
145                 150                 155

(2) INFORMATION FOR SEQ ID NO:14:

-continued

```
    (i) SEQUENCE CHARACTERISTICS:
        (A) LENGTH: 210 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Leu Gly Asp Arg Gly Arg Gly Arg Ala Leu Pro Gly Gly Arg Leu Gly
1               5                   10                  15

Gly Arg Gly Arg Gly Arg Ala Pro Glu Arg Val Gly Gly Arg Gly Arg
            20                  25                  30

Gly Arg Gly Thr Ala Ala Pro Arg Ala Ala Pro Ala Ala Arg Gly Ser
        35                  40                  45

Arg Pro Gly Pro Ala Gly Thr Met Ala Ala Gly Ser Ile Thr Thr Leu
50                  55                  60

Pro Ala Leu Pro Glu Asp Gly Gly Ser Gly Ala Phe Pro Pro Gly His
65                  70                  75                  80

Phe Lys Asp Pro Lys Arg Leu Tyr Cys Lys Asn Gly Gly Phe Phe Leu
                85                  90                  95

Arg Ile His Pro Asp Gly Arg Val Asp Gly Val Arg Glu Lys Ser Asp
            100                 105                 110

Pro His Ile Lys Leu Gln Leu Gln Ala Glu Glu Arg Gly Val Val Ser
        115                 120                 125

Ile Lys Gly Val Cys Ala Asn Arg Tyr Leu Ala Met Lys Glu Asp Gly
130                 135                 140

Arg Leu Leu Ala Ser Lys Cys Val Thr Asp Glu Cys Phe Phe Phe Glu
145                 150                 155                 160

Arg Leu Glu Ser Asn Asn Tyr Asn Thr Tyr Arg Ser Arg Lys Tyr Thr
                165                 170                 175

Ser Trp Tyr Val Ala Leu Lys Arg Thr Gly Gln Tyr Lys Leu Gly Ser
            180                 185                 190

Lys Thr Gly Pro Gly Gln Lys Ala Ile Leu Phe Leu Pro Met Ser Ala
        195                 200                 205

Lys Ser
    210

(2) INFORMATION FOR SEQ ID NO:15:

(i) SEQUENCE CHARACTERISTICS:
        (A) LENGTH: 206 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

Met Ser Gly Pro Gly Thr Ala Ala Val Ala Leu Leu Pro Ala Val Leu
1               5                   10                  15

Leu Ala Leu Leu Ala Pro Trp Ala Gly Arg Gly Gly Ala Ala Ala Pro
            20                  25                  30

Thr Ala Pro Asn Gly Thr Leu Glu Ala Glu Leu Glu Arg Arg Trp Glu
        35                  40                  45

Ser Leu Val Ala Leu Ser Leu Ala Arg Leu Pro Val Ala Ala Gln Pro
50                  55                  60

Lys Glu Ala Ala Val Gln Ser Gly Ala Gly Asp Tyr Leu Leu Gly Ile
65                  70                  75                  80
```

―continued

```
Lys Arg Leu Arg Arg Leu Tyr Cys Asn Val Gly Ile Gly Phe His Leu
                85                  90                  95
Gln Ala Leu Pro Asp Gly Arg Ile Gly Gly Ala His Ala Asp Thr Arg
            100                 105                 110
Asp Ser Leu Leu Glu Leu Ser Pro Val Glu Arg Gly Val Val Ser Ile
        115                 120                 125
Phe Gly Val Ala Ser Arg Phe Phe Val Ala Met Ser Ser Lys Gly Lys
    130                 135                 140
Leu Tyr Gly Ser Pro Phe Phe Thr Asp Glu Cys Thr Phe Lys Glu Ile
145                 150                 155                 160
Leu Leu Pro Asn Tyr Asn Ala Tyr Glu Ser Tyr Lys Tyr Pro Gly
                165                 170                 175
Met Phe Ile Ala Leu Ser Lys Asn Gly Lys Thr Lys Lys Gly Asn Arg
            180                 185                 190
Val Ser Pro Thr Met Lys Val Thr His Phe Leu Pro Arg Leu
        195                 200                 205
```

(2) INFORMATION FOR SEQ ID NO:16:

(i) SEQUENCE CHARACTERISTICS:
        (A) LENGTH: 208 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:16:

```
Met Ala Leu Gly Gln Lys Leu Phe Ile Thr Met Ser Arg Gly Ala Gly
1               5                   10                  15
Arg Leu Gln Gly Thr Leu Trp Ala Leu Val Phe Leu Gly Ile Leu Val
            20                  25                  30
Gly Met Val Val Pro Ser Pro Ala Gly Thr Arg Ala Asn Asn Thr Leu
        35                  40                  45
Leu Asp Ser Arg Gly Trp Gly Thr Leu Leu Ser Arg Ser Arg Ala Gly
    50                  55                  60
Leu Ala Gly Glu Ile Ala Gly Val Asn Trp Glu Ser Gly Tyr Leu Val
65                  70                  75                  80
Gly Ile Lys Arg Gln Arg Arg Leu Tyr Cys Asn Val Gly Ile Gly Phe
                85                  90                  95
His Leu Gln Val Leu Pro Asp Gly Arg Ile Ser Gly Thr His Glu Glu
            100                 105                 110
Asn Pro Tyr Ser Leu Leu Glu Ile Ser Thr Val Glu Arg Gly Val Val
        115                 120                 125
Ser Leu Phe Gly Val Arg Ser Ala Leu Phe Val Ala Met Asn Ser Lys
    130                 135                 140
Gly Arg Leu Tyr Ala Thr Pro Ser Phe Gln Glu Glu Cys Lys Phe Arg
145                 150                 155                 160
Glu Thr Leu Leu Pro Asn Asn Tyr Asn Ala Tyr Glu Ser Asp Leu Tyr
                165                 170                 175
Gln Gly Thr Tyr Ile Ala Leu Ser Lys Tyr Gly Arg Val Lys Arg Gly
            180                 185                 190
Ser Lys Val Ser Pro Ile Met Thr Val Thr His Phe Leu Pro Arg Ile
        195                 200                 205
```

(2) INFORMATION FOR SEQ ID NO:17:

```
    (i) SEQUENCE CHARACTERISTICS:
        (A) LENGTH: 268 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:17:

Met Ser Leu Ser Phe Leu Leu Leu Leu Phe Phe Ser His Leu Ile Leu
1               5                   10                  15

Ser Ala Trp Ala His Gly Glu Lys Arg Leu Ala Pro Lys Gly Gln Pro
                20                  25                  30

Gly Pro Ala Ala Thr Asp Arg Asn Pro Ile Gly Ser Ser Ser Arg Gln
            35                  40                  45

Ser Ser Ser Ser Ala Met Ser Ser Ser Ala Ser Ser Ser Pro Ala
        50                  55                  60

Ala Ser Leu Gly Ser Gln Gly Ser Gly Leu Glu Gln Ser Ser Phe Gln
65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
                100                 105                 110

His Glu Ala Asn Met Leu Ser Val Leu Glu Ile Phe Ala Val Ser Gln
            115                 120                 125

Gly Ile Val Gly Ile Arg Gly Val Phe Ser Asn Lys Phe Leu Ala Met
130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
        195                 200                 205

Gln His Ile Ser Thr His Phe Leu Pro Arg Phe Lys Gln Ser Glu Gln
    210                 215                 220

Pro Glu Leu Ser Phe Thr Val Thr Val Pro Glu Lys Lys Asn Pro Pro
225                 230                 235                 240

Ser Pro Ile Lys Ser Lys Ile Pro Leu Ser Ala Pro Arg Lys Asn Thr
                245                 250                 255

Asn Ser Val Lys Tyr Arg Leu Lys Phe Arg Phe Gly
                260                 265
```